United States Patent [19]

Busnot et al.

[11] Patent Number: 6,136,084
[45] Date of Patent: Oct. 24, 2000

[54] SULPHUR COMPOUNDS COATED WITH A ZINC COMPOUND FOR USE AS PIGMENTS

[75] Inventors: Sylvain Busnot, Maysel; Pierre Macaudiere, Asnières-sur-Seine, both of France

[73] Assignee: Rhodia Chimie, Courbevoie, France

[21] Appl. No.: 09/068,871

[22] PCT Filed: Nov. 22, 1996

[86] PCT No.: PCT/FR96/01853

§ 371 Date: May 20, 1998

§ 102(e) Date: May 20, 1998

[87] PCT Pub. No.: WO97/20002

PCT Pub. Date: Jun. 5, 1997

[30] Foreign Application Priority Data

Nov. 24, 1995 [FR] France .................... 95 13973

[51] Int. Cl.[7] .................. C08K 9/02; C09C 3/06; C09C 1/00
[52] U.S. Cl. .................. 106/419; 106/401; 106/461; 428/403; 428/404
[58] Field of Search .................. 106/419, 401, 106/461; 428/403, 404

[56] References Cited

U.S. PATENT DOCUMENTS

| | | | |
|---|---|---|---|
| 4,147,212 | 4/1979 | Tisdale | 423/232 |
| 4,287,257 | 9/1981 | Ohmatoi et al. | 428/403 |
| 4,331,706 | 5/1982 | Kindrick | 427/74 |
| 5,348,581 | 9/1994 | Chopin et al. | 106/461 |
| 5,401,309 | 3/1995 | Chopin et al. | 106/461 |
| 5,501,733 | 3/1996 | Macaudiere et al. | 106/461 |
| 5,755,868 | 5/1998 | Macaudiere | 106/401 |

FOREIGN PATENT DOCUMENTS

| | | |
|---|---|---|
| 20338 | 12/1986 | European Pat. Off. . |
| 4404953 | 8/1995 | Germany . |

OTHER PUBLICATIONS

Chemical Abstract and Derwent abstracts for DE 4404953, Aug. 1995.
Chemical Absttact citation 114:170,406, abstract for JP 2–307,475 A2, Dec. 1990.
Chemical Abstract citation 68:52991, fukui et al, "Hygienic Chemical Studies of Noxious Gasses. X. Improvement of Absorption Mixture and Examination of the Methylene Blue Method for Determination of Hydrogen Sulfide"; Eisei Kagaku, 13 (1), pp. 16–21, 1967 no month.

*Primary Examiner*—C. Melissa Koslow
*Attorney, Agent, or Firm*—Jean-Louis Seugnet

[57] ABSTRACT

The present invention relates to a composition based on a sulphur compound, zinc and optionally a transparent oxide, to a process for its preparation and to its use as a dye pigment. The composition of the invention is characterized in that it comprises a support based on at least one sulphur compound, and a zinc compound, deposited on the support and obtained by reaction of a zinc precursor with aqueous ammonia and/or an ammonium salt. The composition may also comprise a layer based on at least one transparent oxide deposited at the surface of the support and/or fluorine atoms. It may be prepared in particular by a process in which the support, a zinc precursor, aqueous ammonia and/or an ammonium salt and, if necessary, a transparent oxide precursor and a fluorinating agent are placed in contact and the zinc compound is deposited on the support and, where appropriate, the transparent oxide is precipitated on the said support.

14 Claims, No Drawings

SULPHUR COMPOUNDS COATED WITH A ZINC COMPOUND FOR USE AS PIGMENTS

This application is an application under 35 U.S.C. Section 371 of International Application Number PCT/FR96/01853, filed on Nov. 22, 1996.

The present invention relates to a composition based on a sulphur compound, zinc and optionally a transparent oxide, to a process for its preparation and to its use as a dye pigment.

Inorganic dye pigments are already widely used in many industries, in particular in the paints, plastics and ceramics industries. Among these pigments are found a certain number of sulphur-containing compositions. In particular, products based on rare-earth sulphides have already been proposed by the Applicant as substitutes for pigments comprising metals with reputedly very high toxicity such as, in particular, cadmium, lead, chromium and cobalt, whose use is becoming increasingly severely controlled. Compositions based on sesquisulphides of rare earth and of alkali metal elements have thus been described in EP-A-545,746.

Besides the problem of toxicity in certain cases, sulphur-based pigments generally have the drawback of releasing $H_2S$ in certain applications, for example during their incorporation into media containing traces of water, such as polymers, and most particularly when this incorporation is carried out at a relatively high temperature, for example a temperature of at least 200° C.

There is thus a need for sulphur-based pigments whose release of $H_2S$ is minimized.

The object of the invention is to provide such pigments.

With this aim, the composition according to the invention is characterized in that it comprises:
 a support based on at least one sulphur compound;
 a zinc compound, deposited on the support and obtained by reaction of a zinc precursor with aqueous ammonia and/or an ammonium salt.

According to a specific embodiment of the invention, the composition of the invention is characterized in that it also comprises a layer based on at least one transparent oxide deposited at the surface of the support.

According to another embodiment of the invention, the composition is characterized in that it also comprises fluorine atoms.

The invention also relates to a first process for the preparation of a composition of the above type, which is characterized in that the support, a zinc precursor, aqueous ammonia and/or an ammonium salt and, if necessary, a transparent oxide precursor and a fluorinating agent are placed in contact and the zinc compound is deposited on the support and, where appropriate, the transparent oxide is precipitated on the said support.

The invention also relates to a second process for the preparation of a composition of the above type, which is characterized in that the support is subjected to a fluorination treatment in a first stage, then, in a second stage, the said support thus treated, a zinc precursor, aqueous ammonia and/or an ammonium salt and, if necessary, a transparent oxide precursor are placed in contact and the zinc compound is deposited on the support and, where appropriate, the transparent oxide is precipitated on the said support.

The invention further relates to a third process for the preparation of a composition of the above type, which is characterized in that, in a first step, the support, a zinc precursor, aqueous ammonia and/or an ammonium salt and, if necessary, a transparent oxide precursor are placed in contact and the zinc compound is deposited on the support and, where appropriate, the transparent oxide is precipitated on the said support, then, in a second step, the fluorination treatment is carried out.

The invention moreover relates to a fourth process for the preparation of a composition of the above type, which is characterized in that, in a first step, the support and a transparent oxide precursor are placed in contact and the transparent oxide is precipitated on the said support, then, in a second step, the support thus obtained is placed in contact with a zinc precursor, aqueous ammonia and/or an ammonium salt and the zinc compound is deposited on the support.

Lastly, the invention relates to the use, as dye pigment, of a composition of the above type or as obtained by one of the processes of the type described above.

Other characteristics, details and advantages of the invention will emerge even more fully on reading the description which follows, as well as the various concrete, but in no way limiting, examples intended to illustrate it.

For the rest of the description, the expression rare earth is understood to refer to elements of the group consisting of yttrium and the elements of the Periodic Table of atomic number between 57 and 71 inclusive.

The composition according to the invention firstly contains a support, forming a core, based on at least one sulphur compound. This compound may be, in particular, any compound which can be used for its pigmenting qualities. This sulphur compound may be, in particular, a sulphate or a sulphide. Mention may be made here, as examples of sulphide, of cadmium sulphide or sulphoselenide and mercury sulphide. Mention may also be made of pigments of the "ultramarine" violet 15 CI 77007 and blue 29 CI 77007 type according to the Colour Index classification.

According to a preferred variant, when compositions based on non-toxic elements are sought, the support is selected from the products already described by the Applicant. Thus, the support may be based on a rare-earth sulphide of the type $Ln_2S_3$, Ln being the rare earth, as described in EP-A-203,838.

This support may also be a sulphide of rare earth and of alkali metal. It may more precisely be a sulphide of formula $ALnS_2$ in which A represents at least one alkali metal and Ln at least one rare earth. Mention may be made more particularly of those of the following formulae: $KLaS_2$, $NaCeS_2$.

According to another preferred variant, the sulphide is a rare-earth sesquisulphide which contains at least one alkali-metal and/or alkaline-earth metal element, at least part of which is included in the crystal lattice of the said sesquisulphide. Reference may be made to European patent application U.S. Pat. No. 5,348,581 whose teaching is incorporated here. It may be recalled for this variant that the alkali-metal element may be chosen in particular from lithium, sodium and potassium. Obviously, the sulphide or sesquisulphide may comprise several alkali-metal elements.

The alkali-metal or alkaline-earth metal element is at least partly included in the crystal lattice of the sulphide or sesquisulphide. According to another variant, the alkali-metal or alkaline-earth metal element is essentially or totally included in the crystal lattice.

The sesquisulphide may in particular possess a cubic crystallographic structure of $Th_3P_4$ type, which has lacunae in the cation lattice; this lacunar structure may be symbolized by giving the sesquisulphides the formula $M_{1066}[\ ]_{1.33}S_{16}$ (see in particular on this subject: W. H. Zachariasen, "Crystal Chemical Studies of the 5f-Series of Elements. The $Ce_2S_3$-$Ce_3S_4$ Type of Structure", Acta Cryst., (1949), 2, 57).

The alkali-metal or alkaline-earth metal elements may be introduced into these cationic lacunae, to the saturation point of these lacunae or otherwise. The presence of this element within the sulphide or sesquisulphide may be demonstrated by simple chemical analysis. Moreover, X-ray diffraction analysis shows that there is conservation of the $Th_3P_4$ crystal phase of the sesquisulphide with, in certain cases, a more or less considerable modification of the lattice parameters, which is a function of both the nature and the amount of the alkali-metal or alkaline-earth metal element introduced.

Generally, the amount of alkali-metal or alkaline-earth metal element is not more than 50% of the molar amount of rare earth of the sulphide or of the sesquisulphide.

According to another preferred characteristic, the molar amount of alkali metal or alkaline-earth metal is at least equal to 0.1%, and advantageously between 5% and 50% and more particularly 5 and 20%, of the molar amount of rare earth.

In this variant comprising a sesquisulphide, the rare earth may more particularly be cerium or lanthanum. Even more particularly, the rare-earth sesquisulphide is a cubic $\gamma$-$Ce_2S_3$ sesquisulphide.

Mention may also be made, as rare-earth sulphides which can be used as support within the context of the present invention, of those described in European patent application U.S. Pat. No. 5,348,581, the teaching of which is incorporated here. These rare-earth sulphides comprise at least one alkali-metal element and they consist of whole monocrystalline grains with an average size of not more than 1.5 μm. They are obtained by a process in which at least one rare-earth carbonate or hydroxycarbonate is placed together with at least one compound of an alkali-metal element and they are heated in the presence of at least one gas chosen from hydrogen sulphide and carbon sulphide. These products moreover have an average size (CILAS particle size) which is generally less than 2 μm, more particularly between 0.7 and 1.5 μm. After deagglomeration under mild conditions, the average size may be not more than 1.5 μm and advantageously between 0.3 and 0.8 μm.

The invention comprises various embodiments.

The first embodiment corresponds to the simplest structure of the composition. In this case, the composition only comprises a support with a zinc compound deposited on the support. According to a characteristic of the invention which is common to all the embodiments, this zinc compound is obtained by reaction of a zinc precursor with aqueous ammonia and/or an ammonium salt. Thus, the zinc compound which is formed by the reaction can be deposited directly on the support. The form which this zinc compound takes is not known precisely. However, in certain cases, it may be thought that the zinc is present in the form of a zinc-ammonia complex of formula $Zn(NH_3)_x(A)_y$ in which A represents an anion such as $OH^-$, $Cl^-$, the acetate anion or alternatively a mixture of anions, x being at most equal to 4 and y equal to 2.

In the case of the second embodiment of the invention, the composition also comprises a layer based on at least one transparent oxide, deposited at the surface of the support. As regards a product of this type comprising such a layer, reference may also be made to French patent application U.S. Pat. No. 5,401,309 in the name of the Applicant, the teaching of which is incorporated here.

This peripheral layer coating the support may not be perfectly continuous or homogeneous. However, preferably, the compositions according to this embodiment comprise a layer of transparent oxide of uniform coating and of controlled thickness, this being in such a way as not to adversely affect the original colour of the support before coating.

The term transparent oxide is understood here to refer to an oxide which, once deposited on the support in the form of a relatively thin film, absorbs only very few or none at all of the light rays in the visible range, and does so so as not to mask, or to mask very little, the intrinsic original colour of the said support. In addition, it should be noted that the term oxide, which is used for convenience throughout the present description, should be understood as also covering oxides of the hydrated type.

These oxides, or hydrated oxides, may be amorphous and/or crystalline.

Examples of such oxides which may be mentioned more particularly are silicon oxide (silica), aluminium oxide (alumina), zirconium oxide (zirconia), titanium oxide, zirconium silicate $ZrSiO_4$ (zircon) and rare-earth oxides. According to a preferred variant, the coating layer is based on silica. Even more advantageously, this layer essentially, and preferably solely, consists of silica.

According to a third embodiment of the invention, the composition may contain fluorine atoms.

In this case, as regards the arrangement of the fluorine atoms, reference may also be made to French patent application FR-A-2,706,476 in the name of the Applicant, the teaching of which is incorporated here.

The fluoro compositions may display at least one of the following characteristics:

the fluorine atoms are distributed according to a concentration gradient which decreases from the surface to the core of the said compositions.

the fluorine atoms are mainly distributed at the external periphery of the compositions. The term external periphery is understood here to refer to a thickness of material, measured from the surface of the particle, of about a few hundred angstroms. In addition, the term mainly is understood to mean that more than 50% of the fluorine atoms present in the sesquisulphide are in the said external periphery.

the weight percentage of the fluorine atoms present in the compositions does not exceed 10%, and preferably 5%.

the fluorine atoms are present in the form of fluoro or sulphofluoro compounds, in particular in the form of rare-earth fluorides or rare-earth sulphofluorides (thiofluorides).

Obviously, the invention also relates to the combination of the embodiments which have been described above. Thus, a composition may be envisaged comprising a support with an oxide layer and also comprising fluorine atoms.

In all cases, the zinc is preferably located at the periphery of the particles which constitute the compositions. In particular, for compositions comprising a layer of oxide on the support, it may be included in the layer of oxide or located at the surface of this layer.

The process for the preparation of the compositions of the invention will now be described.

According to a first variant, the process is characterized in that the support, a zinc precursor, aqueous ammonia and/or an ammonium salt and, if necessary, a transparent oxide precursor and a fluorinating agent are placed in contact and the zinc compound is deposited on the support and, where appropriate, the transparent oxide is precipitated on the said support.

According to a second variant, the fluorination treatment is carried out in a first step, then, in a second stage, the support thus treated, a zinc precursor, aqueous ammonia and/or an ammonium salt and, if necessary, a transparent oxide precursor are placed in contact and the zinc compound is deposited on the support and, where appropriate, the transparent oxide is precipitated on the said support.

A third variant of the process may also be envisaged. In this case, in a first step, the support, a zinc precursor, aqueous ammonia and/or an ammonium salt and, if necessary, a transparent oxide precursor are placed in contact and the zinc compound is deposited on the support and, where appropriate, the transparent oxide is precipitated on the said support, then, in a second step, the fluorination treatment is carried out.

Lastly, another variant of the process is possible. In this case, in a first step, the support and a transparent oxide precursor are placed in contact and the transparent oxide is precipitated on the said support, then, in a second step, the support thus obtained is placed in contact with a zinc precursor, aqueous ammonia and/or an ammonium salt and the zinc compound is deposited on the support.

In the case of this last variant, the fluorination treatment may be carried out during one of the abovementioned steps or before the first or after the second step.

As regards, in general, the formation of the layer of oxide on the support and the fluorination treatment, reference may be made to the teaching of the patent applications U.S. Pat. No. 5,401,309 and U.S. Pat. No. 5,501,733 and FR-A-2, 706,476 mentioned above.

More precisely, in the case of the preparation of a composition comprising a layer of transparent oxide, the principle of preparation thus consists essentially in precipitating the oxide on the support. Examples of processes will be given below for the various types of oxide, in which processes the oxide precursor may be an alkoxide.

In the case of silica, mention may be made of the preparation of silica by hydrolysis of an alkyl silicate, by forming a reaction medium by mixing water, alcohol, the support which is then placed in suspension, and optionally a base and an alkali-metal fluoride or an ammonium fluoride which may act as a catalyst for the condensation of the silicate. The alkyl silicate is then introduced. A preparation may also be carried out by reaction of the support, a silicate of the alkali-metal silicate type, and an acid.

In the case of an alumina-based layer, the support, an aluminate and an acid may be reacted, by which reaction alumina is precipitated. This precipitation may also be obtained by placing together and reacting the support, an aluminium salt and a base.

Lastly, the alumina may be formed by hydrolysis of an aluminium alkoxide.

As regards the titanium oxide, it may be precipitated by introducing a titanium salt such as $TiCl_4$, $TiOCl_2$ or $TiOSO_4$, on the one hand, and a base, on the other hand, into an aqueous-alcoholic suspension of the support. The process may also be carried out, for example, by hydrolysis of an alkyl titanate or precipitation of a titanium sol.

Lastly, in the case of a zirconium oxide-based layer, it is possible to co-hydrolyse or co-precipitate a suspension of the cerium support in the presence of an organometallic zirconium compound, for example a zirconium alkoxide such as zirconium isopropoxide.

The fluorination may be carried out according to any technique known per se.

In particular, the fluorinating agent may be liquid, solid or gaseous. Preferably, the process is carried out under treatment conditions in which the fluorinating agent is liquid or gaseous.

As examples of fluorinating agents which are suitable for carrying out the treatment according to the invention, mention may be made more particularly of fluorine $F_2$, alkali-metal fluorides, ammonium fluoride, rare-gas fluorides, nitrogen fluoride $NF_3$, boron fluoride $BF_3$, tetrafluoromethane and hydrofluoric acid HF.

In the case of a treatment under a fluorinating atmosphere, the fluorinating agent may be used pure or diluted in a neutral gas, for example nitrogen.

The reaction conditions are preferably selected such that the said treatment induces fluorination only at the surface of the support (mild conditions). In this respect, a fluorination carried out down to the core of the support does not provide substantially improved results when compared with what is essentially a surface-fluorination. In practice, the progress of the fluorination reaction may be monitored and controlled experimentally, for example, by measuring the change in the increase in mass of the materials (increase in mass induced by the gradual introduction of fluorine).

The zinc precursor may be a zinc oxide or hydroxide which is used in suspension. This precursor may also be a zinc salt, preferably a soluble salt. This may be a salt of inorganic acid such as a chloride, or alternatively a salt of organic acid such as an acetate.

According to a specific variant of the invention, the fluorinating agent is ammonium fluoride.

It is also possible to use both aqueous ammonia and an ammonium salt.

According to an advantageous characteristic, the support, the zinc precursor, the aqueous ammonia and/or the ammonium salt and, if necessary, the transparent oxide precursor and the fluorinating agent are placed in contact in the presence of an alcohol. The alcohol used is generally chosen from aliphatic alcohols such as, for example, butanol or ethanol. The alcohol may in particular be introduced with the zinc precursor in the form of an alcoholic zinc solution.

According to another advantageous variant of the invention, the support, the zinc precursor, the aqueous ammonia and/or the ammonium salt and, if necessary, the transparent oxide precursor and the fluorinating agent are placed in contact in the presence of a dispersing agent. The aim of this dispersing agent is to prevent agglomeration of the particles forming the support during their placing in suspension for the treatments described above. It also makes it possible to work in more concentrated media. It promotes the formation of a homogeneous layer of transparent oxide over all of the particles.

This dispersing agent may be chosen from the group of agents which disperse by a steric effect, and in particular nonionic organosoluble or water-soluble polymers. Dispersing agents which may be mentioned are cellulose and its derivatives, polyacrylamides, polyethylene oxides, polyethylene glycols, polyoxyethylenated polyoxypropylene glycols, polyacrylates, polyoxyethylenated alkylphenols, polyoxyethylenated long-chain alcohols, polyvinyl alcohols, alkanolamides, dispersing agents of the polyvinylpyrrolidone type and compounds based on xanthan gum.

In addition, it may be noted that it may be advantageous to treat the suspension obtained from the mixture of reactants with ultrasound.

Lastly, the product obtained after the operations described above may be washed with water or with alcohol. It may also be air-dried or dried under vacuum.

The present invention also relates to the use, as dye pigments, of the compositions described above or obtained by the above preparation processes.

The compositions or products of the invention in effect possess dyeing power and covering power and are consequently suitable for dyeing many materials, such as plastics, paints and the like. They are most particularly suitable for applications in which they are used at a relatively high temperature and under conditions in which there is a risk of $H_2S$ being released possibly as a result of partial hydrolysis of the sulphur compound.

Thus, and more precisely, they may be used to dye polymers for plastics which may be of the thermoplastic or thermosetting type, these polymers being liable to contain traces of water.

As thermoplastic resins which may be dyed according to the invention, mention may be made, purely by way of illustration, of polyvinyl chloride, polyvinyl alcohol, polystyrene, styrene-butadiene, styrene-acrylonitrile and acrylonitrile-butadiene-styrene (A.B.S.) copolymers, acrylic polymers, in particular polymethyl methacrylate, polyolefins such as polyethylene, polypropylene, polybutene and polymethylpentene, cellulose derivatives such as, for example, cellulose acetate, cellulose acetobutyrate and ethylcellulose, and polyamides including polyamide 6—6.

As regards the thermosetting resins for which the compositions according to the invention are also suitable, mention may be made, for example, of phenolic plastics, aminoaldehyde resins, in particular urea-formaldehyde and melamine-formaldehyde copolymers, epoxy resins and thermosetting polyesters.

Use may also be made of the compositions of the invention in special polymers such as fluoro polymers, in particular polytetrafluoroethylene (P.T.F.E.), polycarbonates, silicone elastomers and polyimides.

In this specific application for dyeing plastics, the compositions of the invention may be used directly in the form of powders. They may also, preferably, be used in a predispersed form, for example by premixing with some of the resin, in the form of a concentrated paste or a liquid, thereby allowing them to be introduced into any stage in the manufacture of the resin.

Thus, the products according to the invention may be incorporated into plastics such as those mentioned above in a weight proportion generally ranging either from 0.01 to 5% (relative to the final product) or from 20 to 70% in the case of a concentrate.

The products of the invention may also be used in the field of paints and stains and more particularly in the following resins: alkyd resins, the most common of which is called glycerophthalic resin; resins modified with long- or short-chain oil; acrylic resins derived from (methyl or ethyl) esters of acrylic and methacrylic acid optionally copolymerized with ethyl, 2-ethylhexyl or butyl acrylate; vinyl resins such as, for example, polyvinyl acetate, polyvinyl chloride, polyvinyl butyral, polyvinyl formal and copolymers of vinyl chloride and of vinyl acetate or of vinylidene chloride; aminoaldehyde or phenolic resins, which are usually modified; polyester resins; polyurethane resins; epoxy resins; silicone resins.

Generally, the products are used in a proportion of from 5 to 30% by weight of the paint, and from 0.1 to 5% by weight of the stain.

Lastly, the products according to the invention may also be suitable for applications in the rubber industry, in particular in floor coverings, in the paper and printing-inks industry and in the cosmetics field, as well as many other uses such as, for example, and with no limitation being implied, dyes, in leathers for their finishing and in laminated coverings for kitchens and other work areas, ceramics and glazes.

The products of the invention may also be used to dye materials based on or obtained from at least one inorganic binder.

This inorganic binder may be chosen from hydraulic binders, aerial binders, plaster and binders of the anhydrous or partially hydrated calcium sulphate type.

The term hydraulic binders is understood to refer to substances having the property of setting and hardening after addition of water, forming water-insoluble hydrates. The products of the invention apply most particularly to the dyeing of cements and, obviously, concretes manufactured from these cements by addition of water, sand and/or gravel thereto.

In the context of the present invention the cement may be, for example, of the aluminous type. This is understood to refer to any cement containing a high proportion either of alumina per se or of aluminate or of both. Mention may be made, by way of example, of cements based on calcium aluminate, in particular those of the Secar type.

The cement may also be of the silicate type and more particularly based on calcium silicate. An example which may be given is the Portland cements and, in cements of this type, Portland cements which are rapid- or very-rapid-setting, white cements, sulphate-resistant cements and those comprising blast furnace slag and/or fly ash and/or meta-kaolin.

Mention may also be made of cements based on calcium sulphate and calcium sulphate hemihydrate, as well as magnesium cements known as Sorel cements.

The products of the invention are also used for dyeing aerial binders, that is to say binders which harden in the open air by the action of $CO_2$, of the calcium or magnesium oxide or hydroxide type.

Lastly, the products of the invention are used for dyeing plaster and binders of the anhydrous or partially hydrated calcium sulphate type ($CaSO_4$ and $CaSO_4.\frac{1}{2}H_2O$).

Finally, the invention relates to compositions of dyed material, in particular of the plastic, paint, stain, rubber, ceramic, glaze, paper, ink, cosmetic product, dye, leather or laminated covering type or of the type based on or obtained from at least one inorganic binder, which comprise, as dye pigment, a composition according to the invention or obtained by a process of the type described above.

Examples will now be given.

EXAMPLES

Tests for measurement of $H_2S$ release by the pigment:

Two tests are given below.

Test 1

15 g of polyamide (PA) 6/6 charged with more than 1% moisture content and 0.375 g of pigment (2.5%) are weighed out and introduced into a jacketed electrochemical cell fitted with a lid and thermostatically set to 75° C.

0.13 ml of deionized water is then introduced, using a graduated pipette, into the reactor, and its inlets are sealed with paraflim®.

The reaction mixture is blended using a Rushton paddle rotating at 700 rpm for 10 min.

100 ml of reaction atmosphere are withdrawn using a sampling pump (Gastec NT 00053A) and a calorimetric indicator tube (Gastec No. 4LL, Prolabo) by piercing the parafilm® with the tube.

The tube is left to react for one minute in accordance with its mode of use and the $H_2S$ content in the reaction chamber is then read directly on the tube (in ppm). The precision is 5 ppm.

Test 2

0.45 ml of double-deionized water is introduced into the above electrochemical cell using a graduated pipette. 10 g of polypropylene powder containing 0.5 g of pigment (5%) are then added into the reactor, and its inlets are sealed with parafilm.

The process is then carried out as for Test 1.

Test 2 is considered as being harder than Test 1. This is due to the fact that larger amounts of water and pigment are present. This larger amount of pigment increases the risks of self-abrasion of the pigment. The use of polypropylene also hardens the test since this polymer is more abrasive than the polyamide.

Chromatic Coordinates

The L*, a* and b* chromatic coordinates are given in the CIE 1976 (L*, a* and b*) system as defined by the Commission Internationale d'Eclairage [International Light Commission] and reported in the Recueil des Normes Frangaises [Compendium of French Standards] (AFNOR), colorimetric colour No. X08-12 X08-14 (1983). As regards the measurements taken on the products and the plastics, they are determined using a colorimeter marketed by the company Pacific Scientific. The nature of the illuminant is D65. The observation surface is a circular pastille of area 12.5 cm$^2$. The observation conditions correspond to viewing at an aperture angle of 10°. In the measurements given, the specular component is excluded.

Injection Into Plastic:

The product is incorporated, in a weight proportion of 0.5%, into polypropylene. Test pieces are formed by injection at 240° C.

The chromatic coordinates are measured against a white background.

Operating Conditions:

The polyvinylpyrrolidone (PVP) is dissolved in ethanol.

The fluorinated or non-fluorinated cerium sulphide is added to this solution. The suspension thus obtained is dispersed using ultrasound and the aqueous ammonia solution is then added, followed by the zinc precursor dissolved in ethanol. The ethyl silicate is introduced continuously over two hours. After introduction of the ethyl silicate, the mixture is matured for two hours. The particles thus obtained are washed with ethanol by filtration and then dried at 50° C. for twelve hours except where otherwise indicated.

Example 1

The reactants are used in the following proportions:

|  | g/kg |
| --- | --- |
| Cerium sulphide | 200 |
| 95% Ethanol | 643 |
| Aqueous ammonia (32%) | 100 |
| Zinc acetate | 20 |
| Ethyl silicate | 32 |
| PVP K10 (Aldrich company) | 5 |
| M = 10000 | |

The cerium sulphide used is a sulphide of cubic γ-structure, doped with lithium in an Li/Ce atomic ratio of 0.1. This sulphide was fluorinated beforehand as follows. 10 g of product are introduced into 100 ml of ammonium fluoride solution (5% by mass).

The pH of the mixture is brought to 8 by addition of aqueous ammonia solution and the medium is left stirring for one hour. The product is next filtered off and then dried in a desiccator under vacuum.

The product thus obtained is treated under the operating conditions given above, using aqueous ammonia.

The product obtained has the following chromatic coordinates:

L*=45.4; a*=54.2; b*=43.6

The following values are obtained after injection into polypropylene:

L*=42.3; a*=49.4; b*=34.9

Measurement of the release of H$_2$S gives the following results:

Test 1: not detected; Test 2: not detected

H$_2$S released after injection into polypropylene at 240° C.: not detected.

Comparative Example 2

Example 1 is repeated, but without addition of zinc acetate.

The product obtained has the following chromatic coordinates:

L*=45.7; a*=49.8; b*=35.6

The following values are obtained after injection into polypropylene:

L=43.5; a*=49.8; b*=36.9

Measurement of the release of H$_2$S gives the following results:

Test 1: 20 ppm; Test 2: >60 ppm (higher than the limit of detection)

H$_2$S released after injection into polypropylene at 240° C.: 10 ppm.

Example 3

The reactants are used in the following proportions:

|  | g/kg |
| --- | --- |
| Cerium sulphide | 200 |
| 95% Ethanol | 647.6 |
| Aqueous ammonia (32%) | 100 |
| Zinc chloride | 15.4 |
| Ethyl silicate | 32 |
| PVP K40 (Aldrich company) | 5 |
| M = 40000 | |

The cerium sulphide is the fluoro sulphide used in Example 1.

The product obtained has the following chromatic coordinates:

L*=47.7; a*=52.4; b*=39

The following values are obtained after injection into polypropylene:

L*=43.8; a*=51.3; b*=39.8

Measurement of the release of H$_2$S gives the following results:

Test 1: not detected. Test 2: not detected.

H$_2$S released after injection into polypropylene at 240° C.: not detected.

Example 4

The process is performed as in Example 3, but the product is dried under vacuum at 180° C. for 5 hours.

The following results are obtained:

Test 1: not detected. Test 2: not detected.

H$_2$S released after injection into polypropylene at 240° C.: not detected.

The chromatic coordinates remain unchanged.

Example 5

The process is performed as in Example 1, replacing the cerium sulphide by the same amount of ultramarine blue pigment.

Measurement of the release of H₂S gives the following results:

Test 1: not detected. Test 2: not detected.

Comparative Example 6

The process is performed as in Example 5, but without addition of zinc acetate.

Measurement of the release of H₂S gives the following results:

Test 1: 20 ppm. Test 2: 30 ppm.

Comparative Example 7

This example relates to the preparation of a product for which the zinc is not deposited on the support by reaction with aqueous ammonia.

The starting material used is the sulphide of cubic γ-structure, doped with lithium and fluorinated, described in Example 1. This product is treated under the operating conditions given above in the introduction to the examples, but without any zinc salt and using aqueous ammonia, in the following proportions:

|  | g/kg |
| --- | --- |
| Cerium sulphide | 200 |
| 95% Ethanol | 653 |
| Aqueous ammonia (32%) | 100 |
| Ethyl silicate | 32 |
| PVP K10 | 5 |

A pigment which has a layer of silica and fluorine atoms is thus obtained.

This pigment is then introduced into an ethanolic solution at a proportion of 100 g/l containing zinc stearate. The stearate/pigment proportion is 10% by weight.

The product is then separated out and dried at 50° C. for 12 hours.

Measurement of the release of H₂S according to Test 2 gives a value of 30 ppm.

Example 8

The process is performed as in Example 1, but the zinc precursor is zinc oxide, predispersed in ethanol, before addition.

The reactants are used in the following proportions:

|  | g/kg |
| --- | --- |
| Cerium sulphide | 200 |
| 95% EtOH | 643 |
| 32% Aqueous ammonia | 100 |
| Zinc oxide | 20 |
| Ethyl silicate | 32 |
| PVP K10 | 5 |

The product obtained has the following chromatic coordinates:

L=45.7
a*=48.9
b*=34.2

The following values are obtained after injection into polypropylene:

L=39
a*=49
b*=37

Measurement of the release of H₂S gives the following results:

Test 1=Test 2=not detected.

Example 9

The process is performed as in Example 1, but the zinc precursor is zinc oxide, predispersed in ethanol, before addition.

The reactants are used in the following proportions:

|  | g/kg |
| --- | --- |
| CeLaS₃ | 200 |
| 95% EtOH | 643 |
| 32% Aqueous ammonia | 100 |
| Zinc oxide | 20 |
| Ethyl silicate | 32 |
| PVP K10 | 5 |

The product obtained has the following chromatic coordinates:

L=65.9
a*=49.1
b*=64

The following values are obtained after injection into polypropylene:

L=61.5
a*=46.5
b*=67.3

Measurement of the release of H₂S gives the following results:

Test 1=Test 2=not detected.

What is claimed is:

1. A composition comprising:
    a support comprising at least one rare-earth sulphide and a layer having at least one transparent oxide deposited at its surface; and
    a zinc compound, obtained and deposited on the support said zinc compound being obtained by reaction of a zinc precursor with aqueous ammonia or an ammonium salt.

2. A composition according to claim 1, wherein the transparent oxide is silica.

3. A composition according to claim 1, further comprising fluorine atoms.

4. A composition according to claim 3 having a core and a surface, wherein the fluorine atoms are distributed according to a gradient which decreases from the surface to the core of the composition.

5. A process for the preparation of a composition comprising:
    a support comprising at least one rare-earth sulphide; and
    a zinc compound, obtained and deposited on the support, said zinc compound being obtained by reaction of a zinc precursor with aqueous ammonia or an ammonium salt, said process comprising the steps of:
    a) placing in contact the support, a zinc compound precursor, aqueous ammonia or an ammonium salt to obtain the zinc compound, and
    b) depositing the zinc compound on the support.

6. A process for the preparation of a composition as defined in claim 1, comprising the steps of:
   a) placing in contact the support, aqueous ammonia or an ammonium salt and a transparent oxide precursor to obtain a transparent oxide, then
   b) precipitating the transparent oxide on said support, then
   c) placing in contact the support with a zinc compound precursor, aqueous ammonia or an ammonium salt to obtain the zinc compound, and then
   d) depositing the zinc compound on the support.

7. A process according to claim 6, wherein the oxide precursor is an alkoxide.

8. A process for the preparation of a composition as defined in claim 3, comprising the steps of:
   a) placing in contact the support, aqueous ammonia or an ammonium salt and a transparent oxide precursor to obtain a transparent oxide, then
   b) precipitating the transparent oxide on said support, then
   c) placing in contact the support with a zinc compound precursor, aqueous ammonia or an ammonium salt to obtain the zinc compound, then
   d) depositing the zinc compound on the support, and
   e) further comprising the step of subjecting the support to a fluorinating treatment.

9. A process according to claim 8, wherein the support, the zinc precursor, the aqueous ammonia or the ammonium salt, the transparent oxide precursor and the fluorinating agent are placed in contact in the presence of an alcohol.

10. A process according to claim 8, wherein in step e) the fluorinating treatment is carried out with ammonium fluoride.

11. A process according to claim 8, wherein the support, the zinc precursor, the aqueous ammonia or the ammonium salt, the transparent oxide precursor and the fluorinating agent are placed in contact in the presence of a dispersing agent.

12. A process according to claim 11, wherein the dispersing agent is a nonionic organo-soluble or water-soluble polymer.

13. A process according to claim 12, wherein the dispersing agent is a polyvinylpyrrolidone polymer.

14. A composition comprising:
   a support comprising at least one rare-earth sulphide and a layer having at least one transparent oxide deposited at its surface; and
   a zinc compound, obtained and deposited on the support, said zinc compound being obtained by reaction of a zinc precursor with aqueous ammonia or an ammonium salt in the presence of a dispersing agent and of an alcohol.

\* \* \* \* \*